United States Patent
Yamakawa et al.

(10) Patent No.: US 12,023,513 B2
(45) Date of Patent: Jul. 2, 2024

(54) LIGHT SOURCE FOR MYOPIA PREVENTION ARTICLE AND METHOD OF USING LIGHT SOURCE FOR MYOPIA PREVENTION ARTICLE

(71) Applicants: TOSHIBA MATERIALS CO., LTD., Yokohama (JP); TSUBOTA LABORATORY, INC., Tokyo (JP)

(72) Inventors: Masahiko Yamakawa, Yokohama (JP); Hidemasa Torii, Tokyo (JP); Toshihide Kurihara, Tokyo (JP); Kazuo Tsubota, Tokyo (JP)

(73) Assignees: Toshiba Materials Co., Ltd., Yokohama (JP); Tsubota Laboratory, Inc., Tokyo (JP)

( * ) Notice: Subject to any disclaimer, the term of this patent is extended or adjusted under 35 U.S.C. 154(b) by 538 days.

(21) Appl. No.: 17/301,859

(22) Filed: Apr. 16, 2021

(65) Prior Publication Data

US 2021/0228901 A1    Jul. 29, 2021

Related U.S. Application Data

(63) Continuation of application No. 16/044,909, filed on Jul. 25, 2018, now Pat. No. 11,007,375, which is a
(Continued)

(30) Foreign Application Priority Data

| Feb. 1, 2016 | (JP) | 2016-017471 |
| Feb. 1, 2016 | (JP) | 2016-017472 |

(51) Int. Cl.
*A61N 5/06* (2006.01)
*A61F 9/00* (2006.01)
(Continued)

(52) U.S. Cl.
CPC ............. *A61N 5/0613* (2013.01); *A61F 9/00* (2013.01); *A61N 5/06* (2013.01);
(Continued)

(58) Field of Classification Search
CPC ............... A61N 5/0613; A61N 5/06; A61N 2005/0651; A61N 2005/0654;
(Continued)

(56) References Cited

U.S. PATENT DOCUMENTS

| 9,074,750 B2 | 7/2015 | Foulds et al. |
| 9,082,939 B2 * | 7/2015 | Yamakawa ............. H01L 33/50 |

(Continued)

FOREIGN PATENT DOCUMENTS

| JP | 2011-181739 A1 | 9/2011 |
| WO | 2007/037120 A1 | 4/2007 |
| WO | 2015/186723 A1 | 12/2015 |

OTHER PUBLICATIONS

Stephen B. Prepas., "Light, Literacy and the Absence of Ultraviolet Radiation in the Development of Myopia", Medical Hypotheses, Eden Press, vol. 70, No. 3, Jan. 1, 2008, pp. 635-637.
(Continued)

*Primary Examiner* — Michael Maskell
(74) *Attorney, Agent, or Firm* — BURR PATENT LAW, PLLC

(57) ABSTRACT

A light source for myopia prevention article includes a light emitter to emit light having an emission spectrum continuing from a first wavelength of not less than 360 nm nor more than 400 nm to a second wavelength of more than 400 nm.

8 Claims, 7 Drawing Sheets

Related U.S. Application Data continuation of application No. PCT/JP2017/003437, filed on Jan. 31, 2017.

(51) Int. Cl.

| | |
|---|---|
| *C09K 11/77* | (2006.01) |
| *F21S 2/00* | (2016.01) |
| *F21V 9/38* | (2018.01) |
| *H01L 25/075* | (2006.01) |
| *H01L 33/50* | (2010.01) |

(52) U.S. Cl.
CPC .. *C09K 11/77342* (2021.01); *C09K 11/77348* (2021.01); *C09K 11/7738* (2013.01); *F21S 2/00* (2013.01); *F21V 9/38* (2018.02); *H01L 25/0753* (2013.01); *H01L 33/50* (2013.01); *H01L 33/504* (2013.01); *A61N 2005/0651* (2013.01); *A61N 2005/0654* (2013.01); *A61N 2005/0663* (2013.01); *A61N 2005/0667* (2013.01)

(58) Field of Classification Search
CPC .... A61N 2005/0663; A61N 2005/0667; A61F 9/00; C09K 11/77342; C09K 11/77348; C09K 11/7738; F21S 2/00; F21V 9/38; H01L 25/0753; H01L 33/50; H01L 33/504
USPC .......... 250/492.1, 504 R; 351/159.65, 159.6, 351/159.01, 41
See application file for complete search history.

(56) References Cited

U.S. PATENT DOCUMENTS

| | | | |
|---|---|---|---|
| 10,133,092 B2* | 11/2018 | Tsubota | G02C 7/04 |
| 2009/0146569 A1 | 6/2009 | Krijnen et al. | |
| 2009/0272985 A1 | 11/2009 | Ishii et al. | |
| 2013/0278887 A1 | 10/2013 | Legerton | |
| 2014/0081357 A1* | 3/2014 | Legerton | F21K 9/23 |
| | | | 607/88 |
| 2015/0018599 A1 | 1/2015 | Legerton | |
| 2017/0168320 A1 | 6/2017 | Tsubota et al. | |

OTHER PUBLICATIONS

Justin C. Sherwin et al., "The Association between Time Spent Outdoors and Myopia Using a Novel Biomarker of Outdoor Light Exposure," *Investigative Ophthalmology & Visual Science*, 2012, vol. 53, No. 8, pp. 4363-4370.
David S. Hammond et al., "Compensation to Positive as Well as Negative Lenses Can Occur in Chicks Reared in Bright Uv Lighting," *Vision Research*, 2012, vol. 67, pp. 44-50.
Hidemasa Torii et al., "Violet Light Exposure Can Be a Preventive Strategy Against Myopia Progression," *EBio Medicine*, [online]; Dec. 16, 2016; <URL: http://www.sciencedirect.com/science/article/pii/S2352396416305862>.
International Search Report and Written Opinion (Application No. PCT/JP2017/003437) dated Apr. 11, 2017.
Japanese Office Action (Application No. 2017-565562) dated Aug. 27, 2019 (with English translation).
John R. Phillips, et al., "Myopia, Light and Circadian Rhythms," *Advances in Ophthalmology*, Mar. 2012, pp. 141-166.

* cited by examiner

LIGHT SOURCE FOR MYOPIA PREVENTION ARTICLE AND METHOD OF USING LIGHT SOURCE FOR MYOPIA PREVENTION ARTICLE

CROSS REFERENCE TO RELATED APPLICATIONS

This application is a continuation of U.S. application Ser. No. 16/044,909, filed Jul. 25, 2018, which in turn is a continuation application of International Application No. PCT/JP2017/003437, filed Jan. 31, 2017, which designated the United States, and is based upon and claims the benefit of priority from Japanese Patent Application Nos. 2016-017471, filed Feb. 1, 2016, and Japanese Patent Application No. 2016-017472, also filed Feb. 1, 2016; the entire contents of all of which are incorporated herein by reference.

FIELD OF THE INVENTION

Embodiments described herein generally relate to a light source for myopia prevention article and a method of using a light source for myopia prevention article.

BACKGROUND OF THE INVENTION

With the recent spread of electric devices such as a smartphone and a tablet terminal, the number of people who develop an eye disease such as myopia is increasing in the world.

As the myopia, for example, refractive myopia or axial myopia can be cited, and the myopia is the axial myopia in many cases. In the axial myopia, the myopia progresses with extension of an axial length, and the extension is irreversible. High myopia due to the progress of the myopia can also cause blindness. Therefore, there is required a myopia prevention method such as a method of preventing the myopia or a method of retarding the progress of the myopia.

DETAILED DESCRIPTION OF THE INVENTION

A light source for myopia prevention article includes a light emitter to emit light having an emission spectrum continuing from a first wavelength of not less than 360 nm nor more than 400 nm to a second wavelength of more than 400 nm.

Hereinafter, an embodiment will be explained with reference to the drawings. Note that the drawings are schematic, and for example, a relationship between a thickness and a planar dimension, a thickness ratio between the layers, and the like may be different from actual ones. In addition, in the embodiment, substantially the same components are denoted by the same reference signs, and explanations are omitted.

A light source for myopia prevention article of the embodiment includes a light emitter capable of emitting light. The light source for myopia prevention article is one of myopia prevention light sources, and a light source capable of emitting light having a characteristic to suppress myopia. As the suppression of the myopia, for example, there can be cited prevention of the myopia, retardation of progress of the myopia, or the like. As the light source for myopia prevention article, for example, there can be cited a medical light irradiation device to be used for medical practice for suppressing the myopia, or the like. Without being limited to the above, the light source for myopia prevention article may be used for light emitting devices such as a display device and a lighting device. Specific examples of the display device and the lighting device will be described later.

The light emitter emits light in response to a power supply voltage to be supplied. The light emitted from the light emitter is, for example, white light. A color temperature of the light emitted from the light emitter is preferably, for example, not less than 2600 K nor more than 7000 K and further not less than 4000 K nor more than 6700 K. The light emitter includes, for example, a light emitting diode element using an LED (Light Emitting Diode). Without being limited to the light emitting diode element, the light emitter may include an incandescent light bulb or a fluorescent light.

Figure 1:
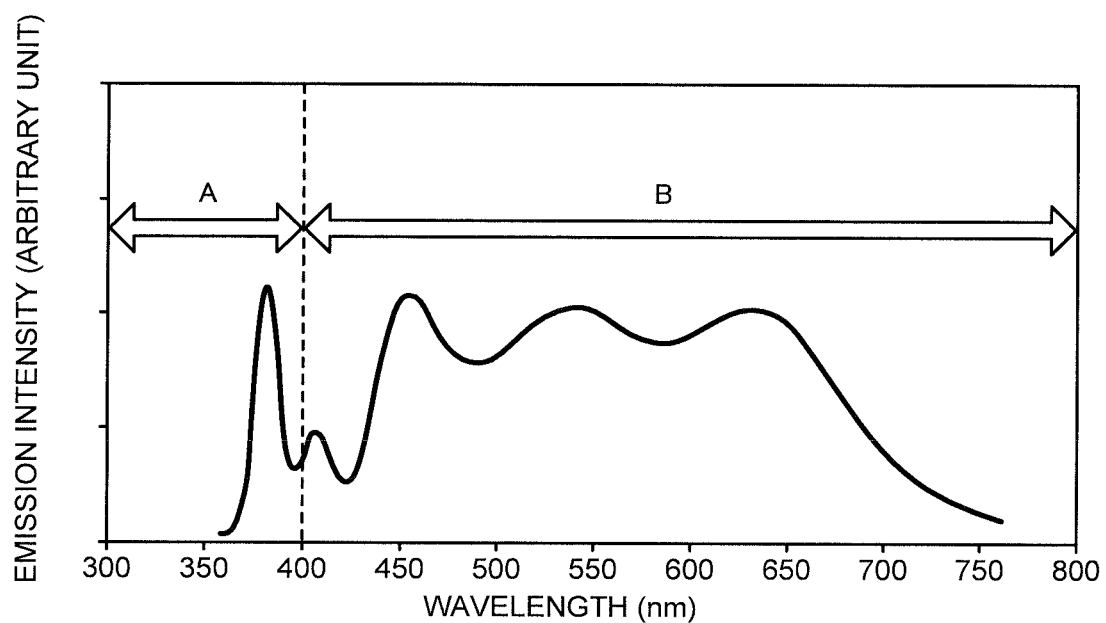
FIG. 1 is a chart illustrating an example of an emission spectrum.

FIG. 1 is a chart illustrating an example of an emission spectrum of the light emitted from the light emitter. A horizontal axis represents a wavelength of the light, and a vertical axis represents relative emission intensity (arbitrary value) of the light. The emission spectrum is measured by, for example, total luminous flux measurement based on a standard of JIS-C-8152.

The emission spectrum illustrated in FIG. 1 has a curved shape continuing from a wavelength of not less than 360 nm nor more than 400 nm to a wavelength of more than 400 nm. In other words, emission intensity of each wavelength from the wavelength of not less than 360 nm nor more than 400 nm to the wavelength of more than 400 nm is more than "0" (zero). That is, the light source for myopia prevention article of the embodiment is capable of emitting the light having the emission intensity over from the wavelength of not less than 360 nm nor more than 400 nm to the wavelength of more than 400 nm.

The emission spectrum may continue from a wavelength of not less than 380 nm nor more than 400 nm to the wavelength of more than 400 nm. The emission spectrum may continue from the wavelength of not less than 380 nm nor more than 400 nm to a wavelength of more than 400 nm and 700 nm or less, and further, more than 400 nm and 750 nm or less. Furthermore, the emission spectrum may continue from the wavelength of not less than 380 nm nor more than 400 nm to a wavelength of 750 nm or more. For example, when the incandescent light bulb is used for the light emitter, the emission spectrum sometimes extends to a wavelength in an infrared region.

The emission spectrum illustrated in FIG. 1 has an emission intensity peak in a wavelength region of 400 nm or less and has a plurality of emission intensity peaks in a wavelength region of more than 400 nm. A wavelength at which the emission intensity of the light is maximum at the emission intensity peak in the wavelength region of 400 nm or less is preferably not less than 360 nm nor more than 400 nm. Note that the emission spectrum may have a plurality of emission intensity peaks in the wavelength region of 400 nm or less. In addition, a wavelength region of not less than 360 nm nor more than 400 nm may have an emission intensity peak with higher emission intensity than that in the wavelength region of more than 400 nm. Furthermore, the emission spectrum may have a broad region in the wavelength region of more than 400 nm.

Without being limited to the above, the emission spectrum need not have the emission intensity peak in the wavelength region of 400 nm or less. A case of having no emission intensity peak is, for example, a case of not having a maximum value in the wavelength region of 400 nm or less but having a spectrum shape in which the emission intensity increases from 360 nm to 400 nm, or the like. In this case, a wavelength at which the emission intensity of the light is maximum in the wavelength region of 400 nm or less is preferably not less than 360 nm nor more than 400 nm.

In the emission spectrum, as illustrated in FIG. 1, emission intensity in a wavelength region of less than 360 nm is preferably "0" (zero). In other words, the emission spectrum preferably has no emission intensity in the wavelength region of less than 360 nm.

Figure 2:
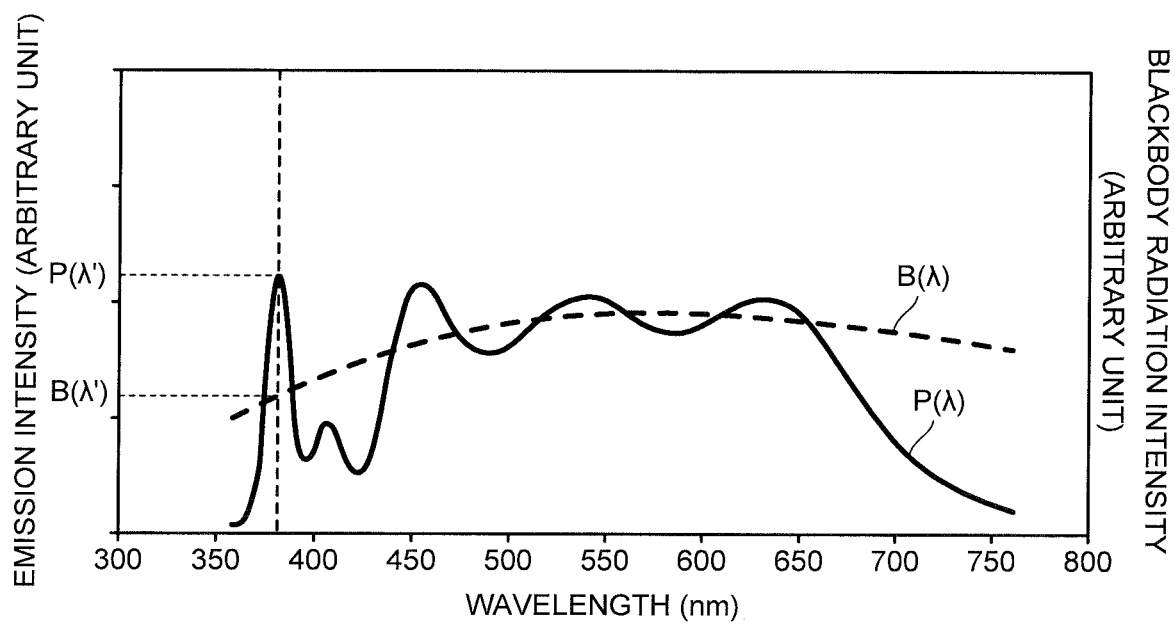
FIG. 2 is a chart illustrating an example of emission spectra.

FIG. 2 is a chart illustrating an example of the emission spectrum of the light emitted from the light emitter and a black body radiation spectrum indicating the same color temperature as that of the above-described light. A horizontal axis represents a wavelength of the light, and a vertical axis represents relative emission intensity (arbitrary value) of each of the light and black body radiation. The emission spectrum is measured by, for example, the total luminous flux measurement based on the standard of JIS-C-8152. The black body radiation is also referred to as a black body emission and corresponds to natural light (sunlight). A color temperature of the natural light is different depending on a time. For example, the color temperature of daytime natural light is about 5100 K, the color temperature of natural light in the morning is about 2700 K to 4200 K, and the color temperature of natural light in the evening is about 2700 K.

The emission spectrum P(λ) illustrated in FIG. 2 has a curved shape continuing from the wavelength in the wavelength region of not less than 360 nm nor more than 400 nm to a wavelength in a visible region of more than 400 nm. In other words, emission intensity of each wavelength from the wavelength in the wavelength region of not less than 360 nm nor more than 400 nm to the wavelength in the visible region of more than 400 nm is more than "0" (zero). That is, the light source for myopia prevention article of the embodiment is capable of emitting the light having the emission intensity over from the wavelength in the wavelength region of not less than 360 nm nor more than 400 nm to the wavelength in the visible region of more than 400 nm.

The emission spectrum P(λ) may continue from the wavelength in the wavelength region of not less than 380 nm nor more than 400 nm to the wavelength in the visible region of more than 400 nm. Further, the emission spectrum P(λ) may continue from the wavelength in the wavelength region of not less than 380 nm nor more than 400 nm to the wavelength of more than 400 nm and 700 nm or less, and further, more than 400 nm and 750 nm or less. Furthermore, the emission spectrum P(λ) may continue from the wavelength in the wavelength region of not less than 380 nm nor more than 400 nm to a wavelength in an infrared region of 750 nm or more. For example, when An incandescent light bulb is used for the light emitter, the emission spectrum P(λ) sometimes extends to the wavelength in the infrared region.

The emission spectrum P(λ) illustrated in FIG. 2 has an emission intensity peak in the wavelength region of 400 nm or less and has a plurality of emission intensity peaks in the visible region of more than 400 nm. A wavelength at which the emission intensity of the light is maximum at the emission intensity peak in the wavelength region is preferably not less than 360 nm nor more than 400 nm. Note that the emission spectrum PQ) may have a plurality of emission intensity peaks in the wavelength region of 400 nm or less. In addition, the wavelength region of not less than 360 nm nor more than 400 nm may have an emission intensity peak with higher emission intensity than that in the visible region of more than 400 nm. Furthermore the emission spectrum P(λ) may have a broad region in the visible region of more than 400 nm.

Without being limited to the above, the emission spectrum P(λ) need not have the emission intensity peak in the wavelength region of 400 nm or less. A case of having no emission intensity peak is, for example, a case of not having a maximum value in the wavelength region of 400 nm or less but having a spectrum shape in which the emission intensity increases from 360 nm to 400 nm, or the like. In this case, a wavelength at which the emission intensity of the light is maximum in the wavelength region of 400 nm or less is preferably not less than 360 nm nor more than 400 nm.

In the emission spectrum, as illustrated in FIG. 2, emission intensity in the wavelength region of less than 360 nm is preferably "0" (zero). In other words, the emission spectrum preferably has no emission intensity in the wavelength region of less than 360 nm.

As illustrated in FIG. 1 and FIG. 2, in the light source for myopia prevention article of the embodiment, the spectrum (P(a)) of the light emitted from the light emitter extends in the wavelength region of not less than 360 nm nor more than 400 nm. Conventionally, it is known that an eye is easily damaged by receiving light including an ultraviolet region such as ultraviolet light. The damage to an eye sometimes causes a decline in eyesight such as myopia. The ultraviolet light can be classified into UVA, UVB, and UVC according to wavelengths. A wavelength range of UVA is not less than 315 nm nor more than 400 nm. A wavelength range of UVB is not less than 280 nm nor more than 315 nm. A wavelength range of UVC is not less than 100 nm nor more than 280 nm.

However, the light from the light source of the embodiment enables reduction of light components in the wavelength region of less than 360 nm and has the emission spectrum (P(λ)) extending in the wavelength region of not less than 360 nm nor more than 400 nm in the wavelength region of 400 nm or less and being in a specific shape, such light can decreases an extension degree of an axial length of a light receiving person smaller compared with, for example, ultraviolet light, visible light, or the like. Accordingly, irradiation with the light allows suppression of the myopia of the light receiving person.

Even though a subject does not wear eyeglasses having a special transmission spectrum, the myopia prevention light source of the embodiment has light characteristics equal to those in an emission spectrum of light transmitted through the eyeglasses. This allows the suppression of the myopia even without wearing the eyeglasses, thereby allowing improvement in convenience.

In order to enhance a suppression effect of the myopia, as illustrated in FIG. 1, in the emission spectrum, a shape of the emission spectrum is preferably regulated so that a ratio a/b of an integrated value a of emission intensity in a wavelength region A of 300 nm to 400 nm to an integrated value b of emission intensity of light in a wavelength region B of 400 nm to 800 nm is more than 0.1 and less than 0.5. The light regulated so that a/b becomes more than 0.1 and less than 0.5 makes it possible not only to reduce the extension degree of the above-described axial length, but also to reduce an adverse effect on a human body and enhance the myopia prevention effect due to a small difference between an emission spectrum of the natural light and that of the regulated light.

Further, in order to enhance the suppression effect of the myopia, the light emitted from the light emitter preferably satisfies $$\int B(\lambda)V(\lambda)d\lambda = \int P(\lambda)V(\lambda)d\lambda \qquad \text{formula 1}$$

($P(\lambda)$ represents the emission spectrum of the light emitted from the light emitter, $B(\lambda)$ represents the black body radiation spectrum indicating the same color temperature as that of the above-described light, and $V(\lambda)$ represents a photopic luminous efficiency spectrum)
and satisfies $$B(\lambda') \leq P(\lambda') \qquad \text{formula 2}$$

($P(\lambda')$ represents a maximum value of emission intensity of the above-described light in a wavelength region of 300 nm to 400 nm and $B(\lambda')$ represents blackbody radiation intensity at a wavelength at which the emission intensity of the above-described light is the above-described maximum value).

The black body radiation spectrum $B(\lambda)$ is found by a Planck distribution. The Planck distribution is found from the following mathematical formula.

$$B(\lambda) = \frac{2hc^2}{\lambda^5} \frac{1}{e^{hc/\lambda kt} - 1} \qquad [\text{Mathematical formula 1}]$$

In the above-described mathematical formula, h represents Planck's constant, c represents the speed of light, $\lambda$ represents a wavelength, e represents a base of natural logarithm, k represents a Boltzmann constant, and T represents a color temperature. In the black body radiation spectrum, h, c, e, and k are constants. Accordingly, determination of the color temperature makes it possible to find an emission spectrum according to a wavelength.

Spectral luminous efficiency is standard spectral luminosity defined by CIE (Commission International de l'Eclairage). The photopic luminous efficiency spectrum $V(\lambda)$ defined by CIE has a maximum peak wavelength at 555 nm and, in addition, has a convex curved shape. It is found from this that a human being can recognize light with a wavelength of about 555 nm at the highest sensitivity.

$P(\lambda) \times V(\lambda)$ indicates the emission intensity of the light source for myopia prevention article in a region of the photopic luminous efficiency spectrum $V(\lambda)$, and $B(\lambda) \times V(\lambda)$ indicates blackbody radiation intensity in the region of the photopic luminous efficiency spectrum $V(\lambda)$. Accordingly, the formula 1 indicates that in the region of the photopic luminous efficiency spectrum $V(\lambda)$, an integrated value of the emission spectrum of the light emitted from the light emitter is the same as an integrated value of the black body radiation spectrum. Further, the formula 2 indicates a comparison between the maximum value $P(\lambda')$ of the emission intensity peak in the wavelength region of not less than 360 nm nor more than 400 nm and the blackbody radiation intensity $B(\lambda')$ at the same wavelength as that at the maximum value $P(\lambda')$.

The light regulated so as to satisfy the formula 1 and the formula 2 makes it possible not only to reduce the extension degree of the above-described axial length, but also to reduce the adverse effect on the human body and enhance the myopia prevention effect due to the small difference between the emission spectrum of the natural light and that of the regulated light. In order to enhance the suppression effect of the myopia, the light emitted from the light emitter more preferably further satisfies $$B(\lambda') \leq P(\lambda') \leq B(\lambda') \times 15. \qquad \text{formula 3}$$

Figure 3:
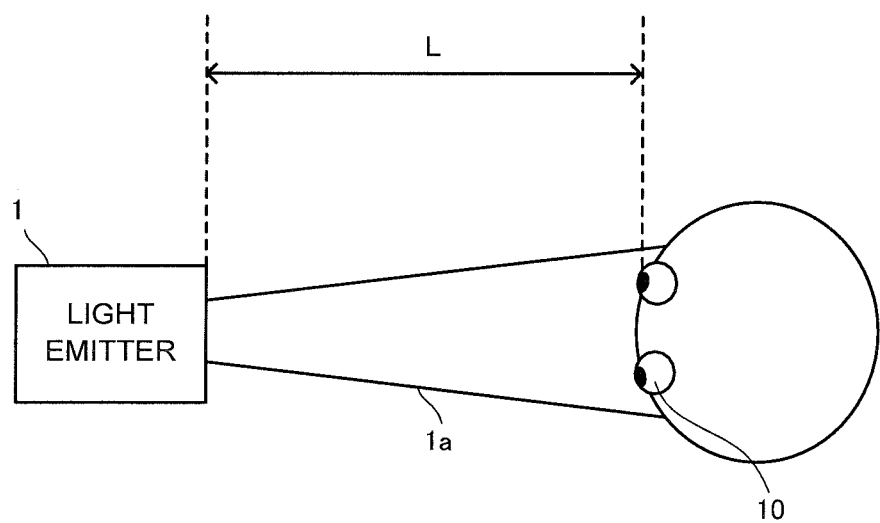
FIG. 3 is a view for explaining an example of a method of using a light source for myopia prevention article.

Next, an example of a method of using the light source for myopia prevention article will be explained. FIG. 3 is a view for explaining the example of the method of using the light source for myopia prevention article. As illustrated in FIG. 3, the example of the method of using the light source for myopia prevention article includes a process of irradiating a portion to be irradiated 10 with a light 1a from a light emitter 1. The portion to be irradiated 10 is, for example, an eye of the light receiving person (mankind or vertebrate animals or the like other than mankind).

In the process of irradiating the portion to be irradiated 10 with the light 1a, an interval L between the light emitter 1 and the portion to be irradiated 10 and a value of a power supply voltage to be supplied to the light emitter 1 are regulated so that an irradiance in a wavelength region of 300 nm to 400 nm except 400 nm of light in the portion to be irradiated 10 becomes not less than 10 µW/cm² nor more than 400 µW/cm². By irradiating the eyes of the light receiving person with the light regulated in the above-described irradiance, the suppression effect of the myopia can be enhanced.

The light source for myopia prevention article of the embodiment makes it possible not only to achieve a high suppression effect of the myopia, but also to emit light close to the emission spectrum of the natural light. Accordingly, the light source for myopia prevention article of the embodiment need not be limited to the medical light irradiation device, but may be used as the light emitting device such as a backlight provided for, for example, the lighting fixture (for example, an interior light, a courtesy light, a cabin light, a street light, a desk lamp, a spot light, or the like) or the display device (for example, a television, a monitor for personal computer, a game machine, a portable media player, a mobile phone, a tablet terminal, a wearable device, 3D eyeglasses, virtual glasses, a mobile book reader, a car navigation system, a digital camera, a car monitor, an aircraft monitor, or the like). The myopia can be suppressed even when light of the light emitting device is received.

Figure 4:
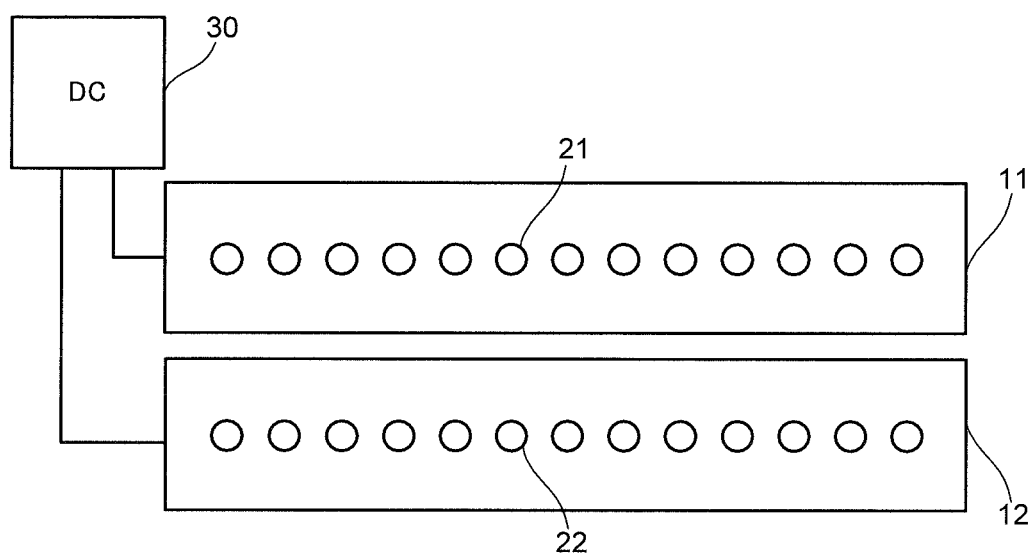
FIG. 4 is a schematic plan view illustrating a configuration example of a light emitter.
Figure 5:
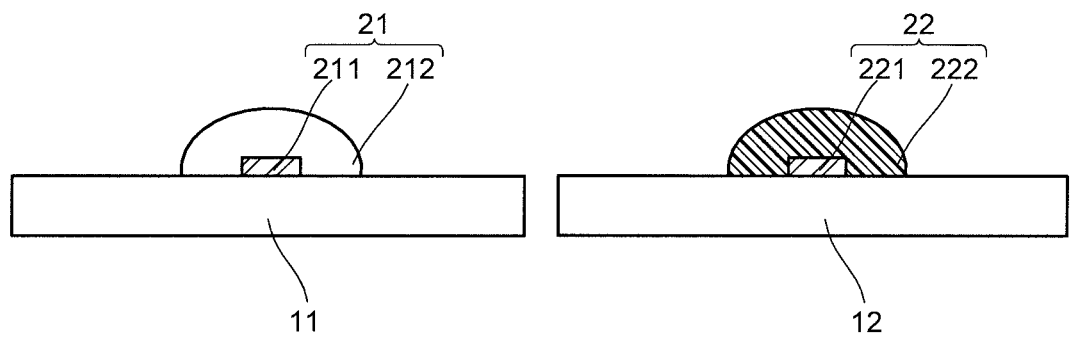
FIG. 5 is a schematic cross-sectional view illustrating the configuration example of the light emitter.

Next, a configuration example of the light emitter 1 will be explained. FIG. 4 is a schematic plan view illustrating a configuration example of one part of the light emitter. FIG. 5 is a schematic cross-sectional view illustrating the configuration example of one part of the light emitter. One part of the light emitter each illustrated in FIG. 4 and FIG. 5 includes a light emitting diode element 21 and a light emitting diode element 22. Note that an incandescent light bulb, a fluorescent lamp, or the like may be used in place of the light emitting diode element 22.

In FIG. 4 and FIG. 5, the light emitting diode element 21 is provided on a substrate 11, and the light emitting diode element 22 is provided on a substrate 12. As the substrate 11 and the substrate 12, for example, an aluminum substrate or the like can be cited. The aluminum substrate is preferable because heat of the light emitting diode element 21 and the light emitting diode element 22 is easily released. Without being limited to the above, another metal substrate, a resin substrate, or the like may be used. When surfaces of the substrate 11 and the substrate 12 have electric conductivity, it is preferable that the light emitting diode element 21 and the light emitting diode element 22 are each mounted, for example, with an insulating film provided on the substrate 11 or the substrate 12 interposed therebetween. The light emitting diode element 21 and the light emitting diode element 22 may be electrically connected with wiring provided on the substrate 11 or the substrate 12, or the substrate 11 or the substrate 12.

The light emitting diode element 21 and the light emitting diode element 22 each emit light in response to the power supply voltage to be supplied from a power supply circuit 30. Values of the power supply voltages necessary for the light emission of the light emitting diode elements 21 and the light emitting diode elements 22 may be different from each other. At this time, separating a substrate mounting the light emitting diode element 21 and a substrate mounting the light emitting diode element 22 from each other makes it easy to supply the power supply voltages with separate values from the power supply circuit 30. Without being limited to the above, the light emitting diode element 21 and the light emitting diode element 22 may be provided on one substrate.

In FIG. 4, the light emitting diode element 21 and the light emitting diode element 22 are each plurally arranged. At this time, a plurality of light emitting diode elements 21 are connected with each other in series or in parallel, and a plurality of light emitting diode elements 22 are connected with each other in series or in parallel. The number of the light emitting diode elements 21 and the number of the light emitting diode elements 22 are not particularly limited, but are appropriately set according to, for example, uses of the light source for myopia prevention article.

An emission spectrum of light emitted from the light emitting diode element 21 preferably has an emission intensity peak in the wavelength region of, for example, not less than 360 nm nor more than 400 nm. The light emitting diode element 21 illustrated in FIG. 5 includes a light emitting diode chip 211 and a layer 212 covering the light emitting diode chip 211.

An emission spectrum of light emitted from the light emitting diode element 22 preferably has an emission intensity peak in the wavelength region of, for example, more than 400 nm. The light emitting diode element 22 illustrated in FIG. 5 includes a light emitting diode chip 221 and a layer 222 covering the light emitting diode chip 221.

An emission spectrum of light emitted from each of the light emitting diode chips 211 and 221 preferably has an emission intensity peak in the wavelength region of, for example, not less than 360 nm nor. As the light emitting diode chips 211 and 221, a chip having a light emitting diode such as, for example, an InGaN-based one, a GaN-based one, or an AlGaN-based one can be used. In the light emitting diode, for example, changing a content of each material, a thickness of each layer, or the like allows regulation of the emission spectrum.

The layer 212 and the layer 222 contain, for example, a silicone resin, an epoxy resin, or the like. In addition, the layer 222 contains a phosphor. The layer containing the phosphor is also referred to as a phosphor layer. The phosphor layer need not contain resin.

The phosphor layer preferably contains three or more phosphors including, for example, a red phosphor, a green to yellow phosphor, and a blue phosphor. The phosphors are each particulate, for example. Types and compounding ratios of the phosphors are each appropriately set according to emission characteristics including a color temperature, an emission spectrum, and the like required of the light emitting diode element. The three or more phosphors are each excited by at least one part of light emitted from the light emitting diode chip to emit light including the wavelength region of more than 400 nm.

Maximum peak wavelengths of the phosphors are preferably different from each other. Making the maximum peak wavelengths of the phosphors different from each other allows a shape of the emission spectrum to be a broad shape in the visible region or the wavelength region of more than 400 nm. Further, in an emission spectrum of light emitted from each of the phosphors, a full width at half maximum of a radiant power peak is preferably 40 nm or more, and further not less than 50 nm nor more than 100 nm.

The phosphor layer preferably contains, for example, the blue phosphor of not less than 58 weight parts nor more than 75 weight parts, the green to yellow phosphor of not less than 3 weight parts nor more than 30 weight parts, and the red phosphor of not less than 2 weight parts nor more than 18 weight parts so as to become a total of 100 weight parts. The above-described mixing ratio makes it possible, for example, to achieve the emission spectrum illustrated in FIG. 1 or FIG. 2.

The emission spectrum of the light emitted from the blue phosphor preferably has an emission intensity peak in a wavelength region of, for example, not less than 430 nm nor more than 460 nm. As the blue phosphor, for example, a europium (Eu)-activated alkaline earth chlorophosphate phosphor having a composition represented by a formula (1) may be used.

$$\text{general formula}: (Sr_{1-x-y-z}Ba_xCa_yEu_z)_5(PO_4)_3 \cdot Cl \tag{1}$$

(In the formula, x, y, and z are numbers satisfying $0 \le x < 0.5$, $0 \le y < 0.1$, and $0.005 \le z < 0.1$)

The emission spectrum of the light emitted from the green to yellow phosphor preferably has an emission intensity peak in a wavelength region of, for example, not less than 490 nm nor more than 580 nm. As the green to yellow phosphor, for example, at least one selected from a europium (Eu) and manganese (Mn)-activated alkaline earth aluminate phosphor having a composition represented by a formula (2), a europium (Eu) and manganese (Mn)-activated alkaline earth silicate phosphor having a composition represented by a formula (3), a cerium (Ce)-activated rare-earth aluminate phosphor having a composition represented by a formula (4), a europium (Eu)-activated sialon phosphor having a composition represented by a formula (5), and a europium (Eu)-activated sialon phosphor having a composition represented by a formula (6) may be used.

$$\text{general formula}: (Ba_{1-x-y-z}Sr_xCa_yEu_z)(Mg_{1-u}Mn_u)Al_{10}O_{17} \tag{2}$$

(In the formula, x, y, z, and u are numbers satisfying $0 \le x < 0.2$, $0 \le y < 0.1$, $0.005 < z < 0.5$, and $0.1 < u < 0.5$)

$$\text{general formula}: (Sr_{1-x-y-z-u}Ba_xMg_yEu_zMn_u)_2SiO_4 \tag{3}$$

(In the formula, x, y, z, and u are numbers satisfying $0.1 \le x \le 0.35$, $0.025 \le y \le 0.105$, $0.025 \le z \le 0.25$, and $0.0005 \le u \le 0.02$)

$$\text{general formula}: RE_3A_xAl_{5-x-y}B_yO_{12}:Ce_z \tag{4}$$

(In the formula, RE represents at least one element selected from Y, Lu, and Gd, A and B are elements making a pair, (A, B) is any of (Mg, Si), (B, Sc), and (B. In), and x, y, and z are numbers satisfying x<2, y<2, 0.9≤x/y≤1.1, and 0.05≤z≤0.5)

$$\text{general formula:} (Si,Al)_6(O,N)_8:Eu_x \quad (5)$$

(In the formula, x is a number satisfying 0<x<0.3)

$$\text{general formula:} (Sr_{1-x}Eu_x)_\alpha Si_\beta Al_\gamma O_\delta N\omega \quad (6)$$

(In the formula, x, α, β, γ, δ, and ω are numbers satisfying 0<x<1, 0<α≤3, 12≤β≤14, 2≤γ≤3.5, 1≤δ≤3, and 20≤ω≤22)

The emission spectrum of the light emitted from the red phosphor preferably has an emission intensity peak in a wavelength region of, for example, not less than 580 nm nor more than 630 nm. As the red phosphor, for example, at least one selected from a europium (Eu) and bismuth (Bi)-activated yttrium oxide phosphor having a composition represented by a formula (7), a europium-activated alkaline earth nitridoaluminosilicate phosphor having a composition represented by a formula (8), and a europium (Eu)-activated sialon phosphor having a composition represented by a formula (9) may be used.

$$\text{general formula:} (Y_{1-x-y}Eu_xBi_y)_2O_3 \quad (7)$$

(In the formula, x and y are numbers satisfying 0.01≤x<0.15 and 0.001≤y<0.05)

$$\text{general formula:} (Ca_{1-x-y}Sr_xEu_y)SiAlN_3 \quad (8)$$

(In the formula, x and y are numbers satisfying 0≤x<0.4 and 0<y<0.5)

$$\text{general formula:} (Sr_{1-x}Eu_z)_\alpha Si_\beta Al_\gamma O_\delta N_\omega \quad (9)$$

(In the formula, x, α, β, γ, δ, and ω are numbers satisfying 0<x<1, 0<α, ≤3, 5≤β≤9, 1≤γ≤5, 0.5≤δ≤2, and 5≤ω≤15)

Figure 6:
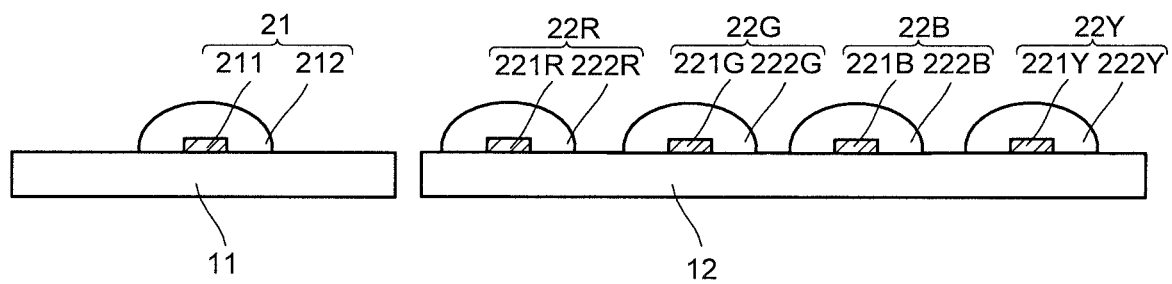
FIG. 6 is a schematic cross-sectional view illustrating another configuration example of the light emitter.
Figure 7:
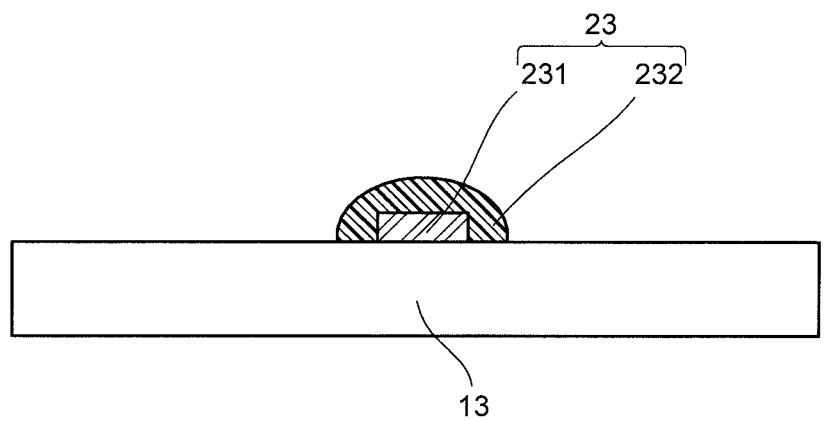
FIG. 7 is a schematic cross-sectional view illustrating the other configuration example of the light emitter.

A configuration of the light emitter is not limited to the configurations illustrated in FIG. 4 and FIG. 5. FIG. 6 and FIG. 7 are schematic cross-sectional views illustrating the other configuration examples of one part of the light emitter.

One part of the light emitter illustrated in FIG. 6 is different compared with the light emitter each illustrated in FIG. 4 and FIG. 5 in a configuration including a light emitting diode element 22R, a light emitting diode element 22G, a light emitting diode element 22B, and a light emitting diode element 22Y on an insulating surface of the substrate 12 as the light emitting diode element 22. Light emitted from the light emitting diode element 22R, light emitted from the light emitting diode element 22G, light emitted from the light emitting diode element 22Y, or light emitted from the light emitting diode element 22B has an emission intensity peak in the wavelength region of more than 400 nm. Note that it is sufficient that the light emitting diode elements 22 include at least one of the light emitting diode element 22R, the light emitting diode element 22G, the light emitting diode element 22B, and the light emitting diode element 22Y. Further, a white light emitting diode element obtained by combining the light emitting diode element 22B and a yellow phosphor may be used.

The light emitting diode element 22R has a light emitting diode chip 221R and a layer 222R covering the light emitting diode chip 221R. As the light emitting diode chip 221R, a chip including a light emitting diode capable of emitting red light can be cited. An emission spectrum of light emitted from the light emitting diode chip 221R (light emitted from the light emitting diode element 22R) preferably has an emission intensity peak in the wavelength region of, for example, not less than 580 nm nor more than 630 nm.

The light emitting diode element 22G has a light emitting diode chip 221G and a layer 222G covering the light emitting diode chip 221G. As the light emitting diode chip 221G, a chip including a light emitting diode capable of emitting green light can be cited. An emission spectrum of light emitted from the light emitting diode chip 221G (light emitted from the light emitting diode element 22G) preferably has an emission intensity peak in the wavelength region of, for example, not less than 490 nm nor more than 580 nm.

The light emitting diode element 22Y has a light emitting diode chip 221Y and a layer 222Y covering the light emitting diode chip 221Y. As the light emitting diode chip 221Y, a chip including a light emitting diode capable of emitting yellow light can be cited. An emission spectrum of light emitted from the light emitting diode chip 221Y (light emitted from the light emitting diode element 22Y) preferably has an emission intensity peak in a wavelength region of, for example, not less than 550 nm nor more than 580 nm.

The light emitting diode element 22B has a light emitting diode chip 221B and a layer 222B covering the light emitting diode chip 221B. As the light emitting diode chip 221B, a chip including a light emitting diode capable of emitting blue light can be cited. An emission spectrum of light emitted from the light emitting diode chip 221B (light emitted from the light emitting diode element 22B) preferably has an emission intensity peak in the wavelength region of, for example, not less than 430 nm nor more than 460 nm.

Each of the layer 222R, the layer 222G, the layer 222Y, and the layer 222B contains a silicone resin, an epoxy resin, or the like. Each of the layer 222R, the layer 222G, the layer 222Y, and the layer 222B need not contain a phosphor. Regarding the other explanations, the explanation of the layer 222 can be appropriately quoted.

The light emitter illustrated in FIG. 7 is different compared with the light emitter illustrated in FIG. 5 in a configuration including a light emitting diode element 23 provided on a substrate 13 in place of the light emitting diode element 21 and the light emitting diode element 22. Regarding an explanation of the substrate 13, the explanation of the substrate 11 or the substrate 12 can be appropriately quoted.

The light emitting diode element 23 has a light emitting diode chip 231 and a layer 232 covering the light emitting diode chip 231 and containing the above-described blue phosphor, the above-described green to yellow phosphor, the above-described red phosphor, and the above-described resin. The three or more phosphors are each excited by one part of light emitted from the light emitting diode chip 231 to emit light including the wavelength region of more than 400 nm. Regarding the other explanations of the phosphors and the resin, the above-described explanation can be appropriately quoted.

An emission spectrum of the light emitted from the light emitting diode chip 231 preferably has an emission intensity peak in the wavelength region of, for example, not less than 360 nm nor more than 400 nm. An emission spectrum of the light emitted from the three or more phosphors preferably has an emission intensity peak in the wavelength region of, for example, more than 400 nm.

The layer 232 is capable of transmitting another one part of the light of the light emitting diode chip 231. Accordingly, an emission spectrum of light emitted from the light emitting diode element 23 has a first emission intensity peak in the wavelength region of not less than 360 nm nor more than 400 nm and has a second emission intensity peak in the wavelength region of more than 400 nm.

In order to transmit another one part of the light of the light emitting diode chip 231, for example, the layer 232 is preferably thinned. A thickness of the layer 232 is preferably, for example, not less than 300 μm nor more than 1000 μm. In addition, in order to transmit another one part of the light of the light emitting diode chip 231, it is preferable to regulate an average particle size (a median of particle size distribution (D50)) of phosphor particles contained in the layer 232. The average particle size of phosphor particles is preferably, for example, not less than 10 μm nor more than 50 m.

The spectrum of the light emitted from the light emitter including the configuration each illustrated in FIG. 4 to FIG. 7 is regulated so as to continue from the wavelength in the wavelength region of not less than 360 nm nor more than 400 nm to the wavelength in the wavelength region of more than 400 nm and so that the emission spectrum extending in the wavelength region of not less than 360 nm nor more than 400 nm has the specific shape as illustrated in FIG. 1, or so as to continue from the wavelength in the above-described wavelength region of not less than 360 nm nor more than 400 nm to the wavelength in the visible region of more than 400 nm and so that the emission spectrum extending in the wavelength region of not less than 360 nm nor more than 400 nm has the specific shape and the above-described light satisfies the formula 1 and the above-described formula 2 as illustrated in FIG. 2. Accordingly, the irradiation with the light from the light emitter allows the suppression of the myopia of the light receiving person. Further, as illustrated in FIG. 1, in the emission spectrum, by regulating the ratio a/b of the integrated value a of the emission intensity in the wavelength region A of 300 nm to 400 nm to the integrated value b of the emission intensity of the light in the wavelength region B of 400 nm to 800 nm, the myopia prevention effect can be enhanced. Note that a configuration of the light emitter is not limited to the configuration each illustrated in FIG. 4 to FIG. 7.

EXAMPLES

Example 1

A light source for myopia prevention article including an ultraviolet lamp, a cool white fluorescent lamp, a power supply, a control circuit which regulated an output of each of the lamps, and an envelope was produced.

The ultraviolet lamp has the same structure as that of a commercially available ultraviolet lamp (for example, model number FL10BLB manufactured by TOSHIBA LIGHTING & TECHNOLOGY CORPORATION). The ultraviolet lamp has a glass tube having a phosphor film on an inner surface thereof. The phosphor film contains a barium silicate phosphor as a near-ultraviolet light emitting material. An emission spectrum obtained by measuring light emitted from the above-described ultraviolet lamp had a peak wavelength at a wavelength of 365 nm and continued from a first wavelength of 340 nm to a second wavelength of 410 nm.

The fluorescent lamp has the same structure as that of a commercially available fluorescent lamp (for example, model number FL20SS manufactured by TOSHIBA LIGHTING & TECHNOLOGY CORPORATION). The fluorescent lamp has white light emitting materials containing a europium-activated alkaline earth phosphate phosphor of 1 weight part as a blue phosphor, a cerium and terbium co-activated lanthanum phosphate phosphor (a common name LAP) of 35 weight parts as a green to yellow phosphor, and a europium-activated yttrium oxide phosphor of 64 weight parts as a red phosphor. A color temperature of white light emitted from the above-described fluorescent lamp was 5000 K.

Figure 8:
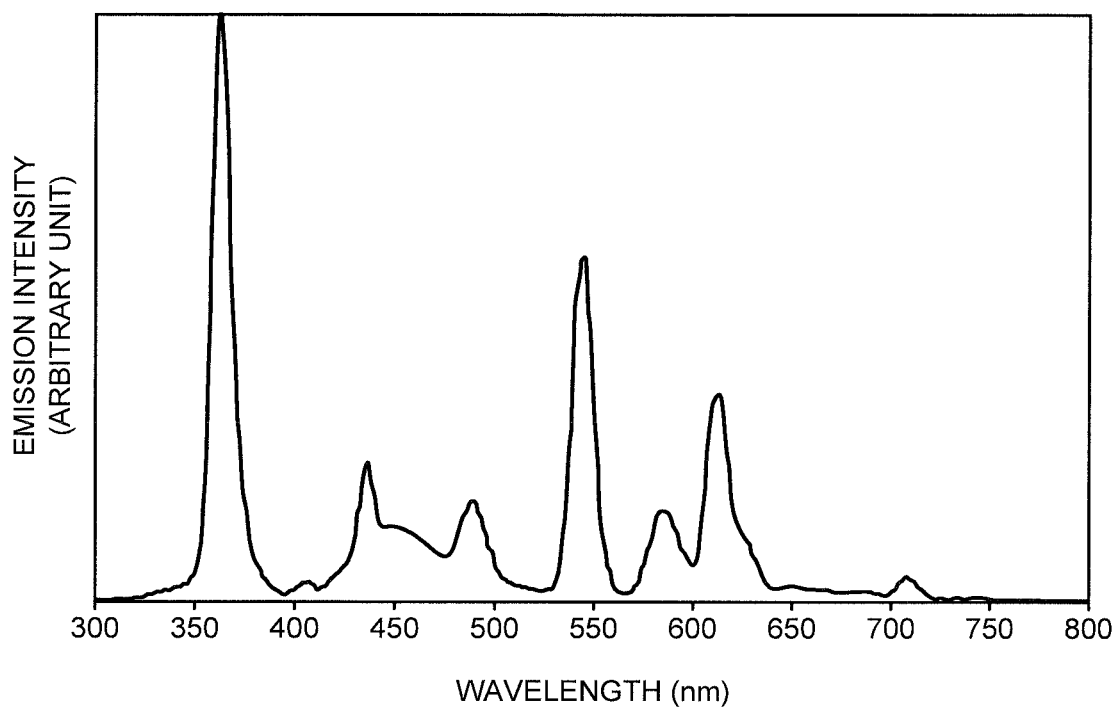
FIG. 8 is a chart illustrating an emission spectrum.

In an emission spectrum of light emitted from the light source for myopia prevention article in Example 1, an output ratio between the ultraviolet lamp and the fluorescent lamp was regulated so that a ratio a/b of an integrated value a of emission intensity in a wavelength region A of 300 nm to 400 nm to an integrated value b of emission intensity of light in a wavelength region B of 400 nm to 800 nm became 0.45. FIG. 8 illustrates an emission spectrum of light emitted from the light source for myopia prevention article at this time.

Figure 9:
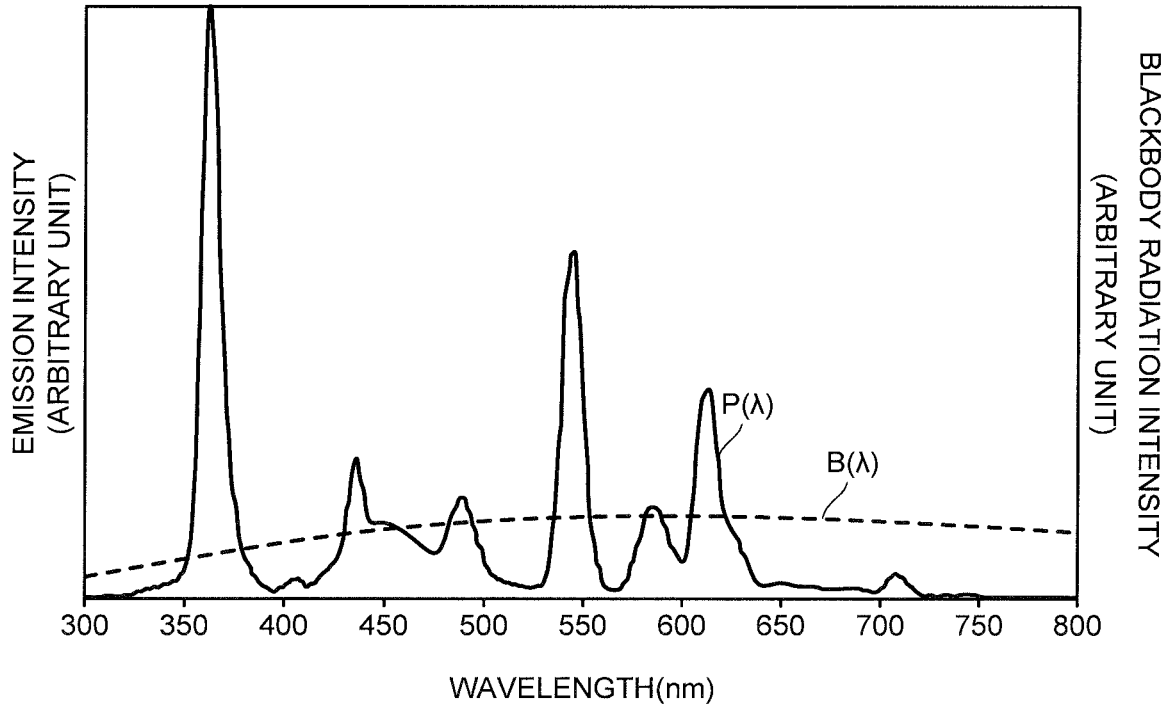
FIG. 9 is a chart illustrating emission spectra.

The output ratio between the ultraviolet lamp and the fluorescent lamp was regulated so that the light emitted from the light source for myopia prevention article in Example 1 satisfied a formula: $\int B(\lambda)V(\lambda)d\lambda = \int P(\lambda)V(\lambda)d\lambda$ and satisfied a formula 2: $B(\lambda') \times 13.6 = P(\lambda')$. FIG. 9 illustrates the emission spectrum of the light emitted from the light source for myopia prevention article at this time and a black body radiation spectrum indicating the same color temperature as that of the above-described light.

In the above-described light source for myopia prevention article, two types of the light emitted from the fluorescent lamp and the light emitted from the ultraviolet lamp are mixed with each other. However, an effect of the light emitted from the ultraviolet lamp on a color temperature of the light emitted from the light source for myopia prevention article is ignored. Consequently, the color temperature of the light emitted from the above-described light source for myopia prevention article is 5000 K the same as that of the fluorescent lamp.

The myopia prevention light source in Example 1 was disposed in a position 30 cm apart from an eye to be examined, and light emitted from the myopia prevention light source was regulated so that an irradiance in a wavelength region of 300 nm to 400 nm except 400 nm became 100 μW/cm² in an irradiated portion of the eye to be examined. Irradiating the eye to be examined with the above-described regulated light made it possible to confirm the suppression effect of the myopia indicated in the embodiment.

Example 2

A light source for myopia prevention article including a light emitting diode element, a power supply, a control circuit which regulated an output of the light emitting diode element, and an envelope was produced.

The light emitting diode element has a GaN-based light emitting diode chip and a layer covering the GaN-based light emitting diode chip and containing light emitting materials. An emission spectrum of light emitted from the light emitting diode element has a peak wavelength at 380 nm and continues from 365 nm to 410 nm.

The layer containing the light emitting materials contains a europium-activated alkaline earth phosphate phosphor of 72 weight parts as a blue phosphor, a europium and manganese co-activated alkaline earth magnesium silicate phosphor of 21 weight parts as a green to yellow phosphor, and a europium-activated calcium nitridoaluminosilicate phosphor of 7 weight parts as a red phosphor.

The layer containing the light emitting materials transmits one part of light emitted from the GaN-based light emitting diode chip. Accordingly, light emitted from the light source for myopia prevention article in Example 2 includes a first light component emitted from the GaN-based light emitting diode chip and a second light component excited by the layer containing the light emitting materials. At this time, an intensity ratio between the first light component and the second light component varies depending on a thickness of the layer containing the light emitting materials. Further, a color temperature of the light emitted from the light source for myopia prevention article in Example 2 was unlikely to vary even though the intensity ratio between the first light component and the second light component varied, resulting in about 5000 K.

Figure 10:
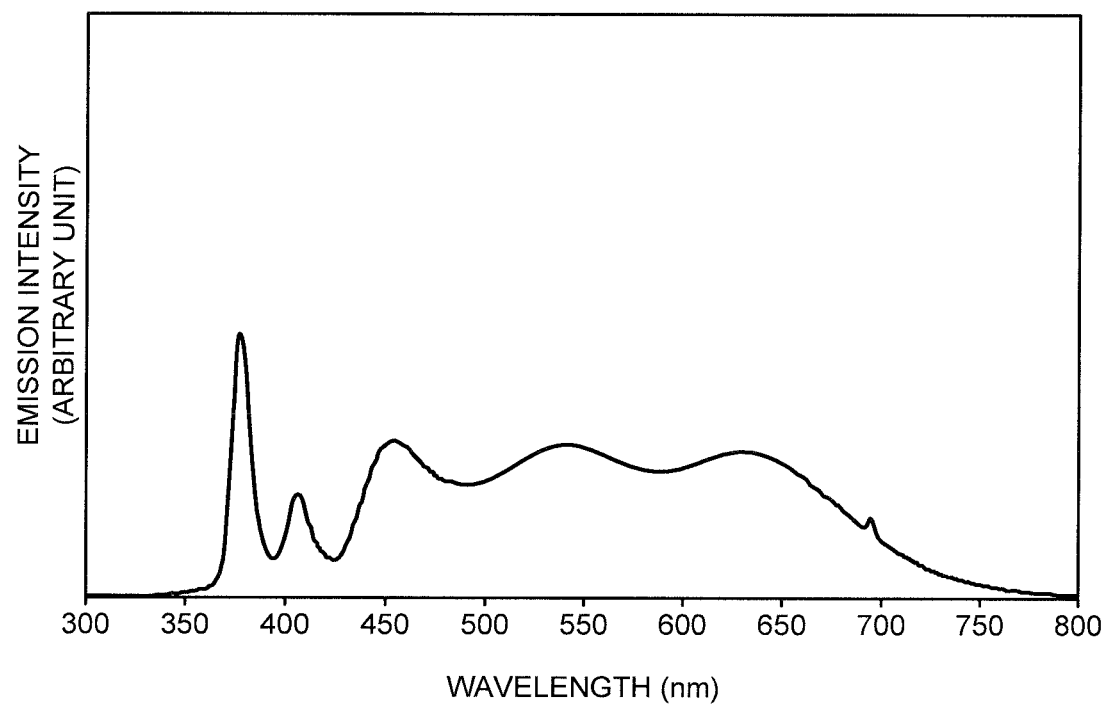
FIG. 10 is a chart illustrating an emission spectrum.

In an emission spectrum of the light emitted from the light source for myopia prevention article in Example 2, the thickness of the layer containing the light emitting materials was regulated so that a ratio a/b of an integrated value a of emission intensity in a wavelength region A of 300 nm to 400 nm to an integrated value b of emission intensity of light in a wavelength region B of 400 nm to 800 nm became 0.10. FIG. 10 illustrates an emission spectrum of light emitted from the light source for myopia prevention article at this time.

Figure 11:
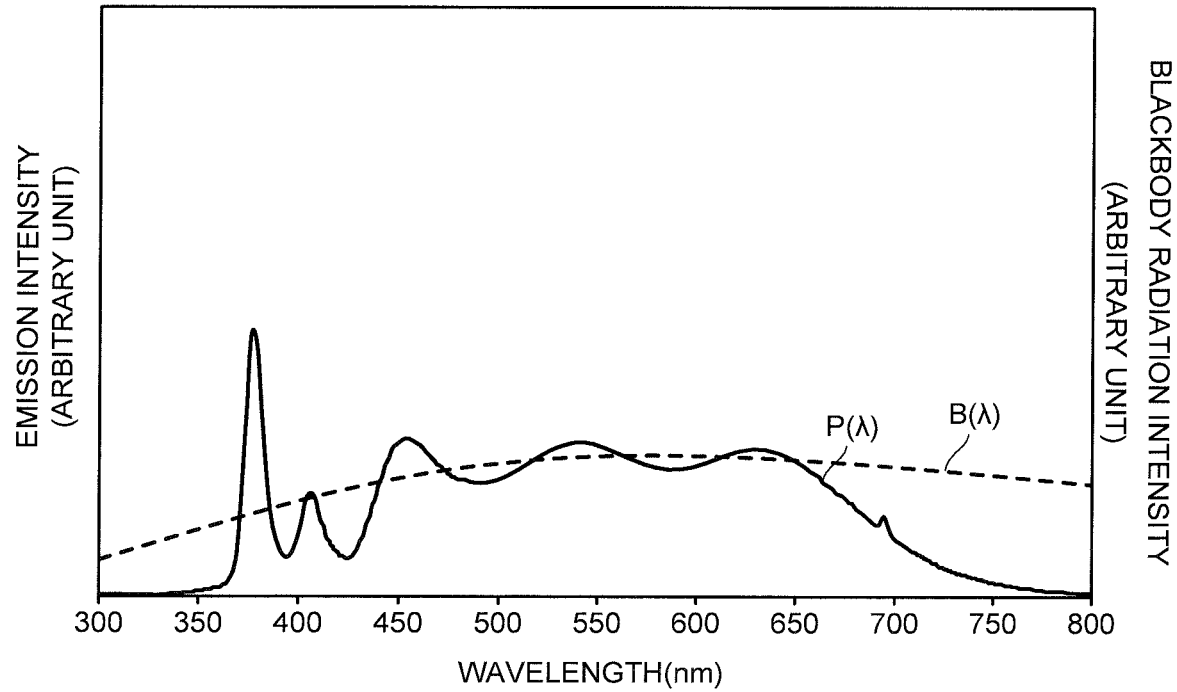
FIG. 11 is a chart illustrating emission spectra.

The thickness of the layer containing the light emitting materials was regulated so that the light emitted from the light source for myopia prevention article in Example 2 satisfied the formula: $\int B(\lambda)V(\lambda)d\lambda = \int P(\lambda)V(\lambda)d\lambda$ and satisfied a formula 2: $B(\lambda') \times 3.2 = P(\lambda')$. FIG. 11 illustrates the emission spectrum of the light emitted from the light source for myopia prevention article at this time and a black body radiation spectrum indicating the same color temperature as that of the above-described light.

The myopia prevention light source in Example 2 was disposed in a position 30 cm apart from an eye to be examined, and light emitted from the myopia prevention light source was regulated so that an irradiance in a wavelength region of 300 nm to 400 nm except 400 nm became 46 $\mu W/cm^2$ in an irradiated portion of the eye to be examined. Irradiating the eye to be examined with the above-described regulated light made it possible to confirm the suppression effect of the myopia indicated in the embodiment.

Example 3

A light source for myopia prevention article including a first light emitting diode element, a second light emitting diode element, a power supply, a control circuit which regulated an output of each of the first and second light emitting diode elements, and an envelope was produced.

The first light emitting diode element has a first GaN-based light emitting diode chip. Light emitted from the first light emitting diode element has a peak wavelength at 380 nm and continues from 365 nm to 410 nm.

The second light emitting diode element has a second GaN-based light emitting diode chip and a layer covering the GaN-based light emitting diode chip and containing light emitting materials. Light emitted from the second light emitting diode element has a peak wavelength at 400 nm.

The layer containing the light emitting materials contains a europium-activated alkaline earth phosphate phosphor of 72 weight parts as a blue phosphor, a europium and manganese co-activated alkaline earth magnesium silicate phosphor of 21 weight parts as a green to yellow phosphor, and a europium-activated calcium nitridoaluminosilicate phosphor of 7 weight parts as a red phosphor.

Light emitted from the light source for myopia prevention article in Example 3 includes a light component excited by the layer containing the light emitting materials as a main component. Further, a color temperature of the light emitted from the light source for myopia prevention article in Example 3 was about 5000 K.

Figure 12:
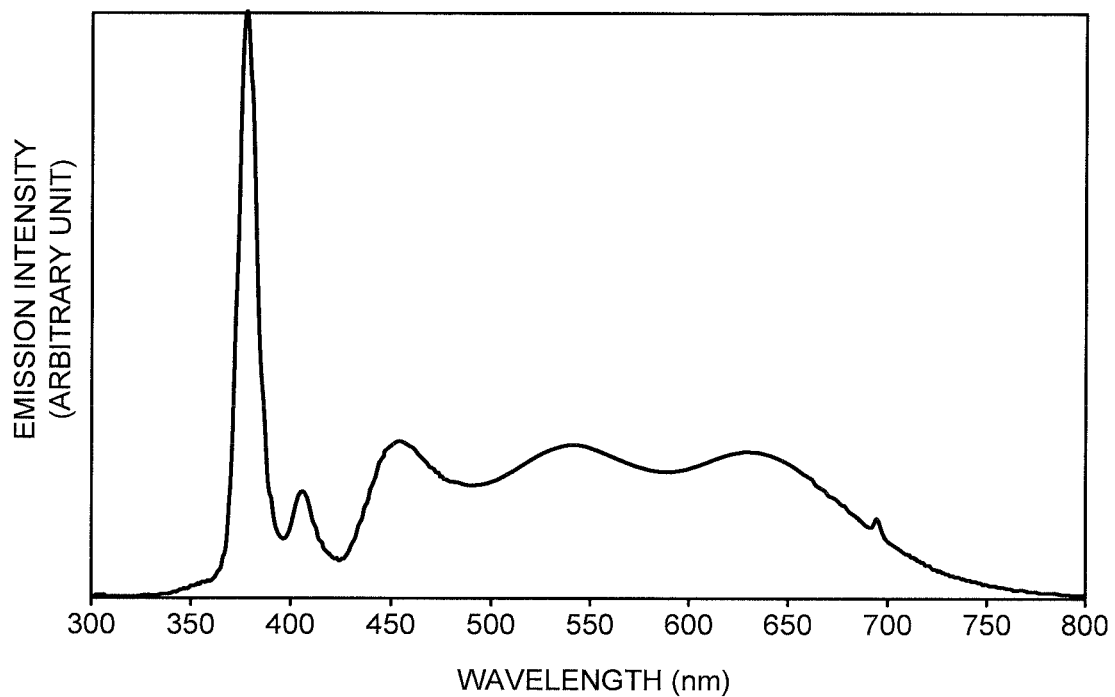
FIG. 12 is a chart illustrating an emission spectrum.

In an emission spectrum of the light emitted from the light source for myopia prevention article in Example 3, an output ratio between the first light emitting diode element and the second light emitting diode element was regulated so that a ratio a/b of an integrated value a of emission intensity in a wavelength region A of 300 nm to 400 nm to an integrated value b of emission intensity of light in a wavelength region B of 400 nm to 800 nm became 0.45. FIG. 12 illustrates an emission spectrum of light emitted from the light source for myopia prevention article at this time. Note that a value of a/b is controlled by, for example, regulating a thickness of the layer containing the light emitting materials.

Figure 13:
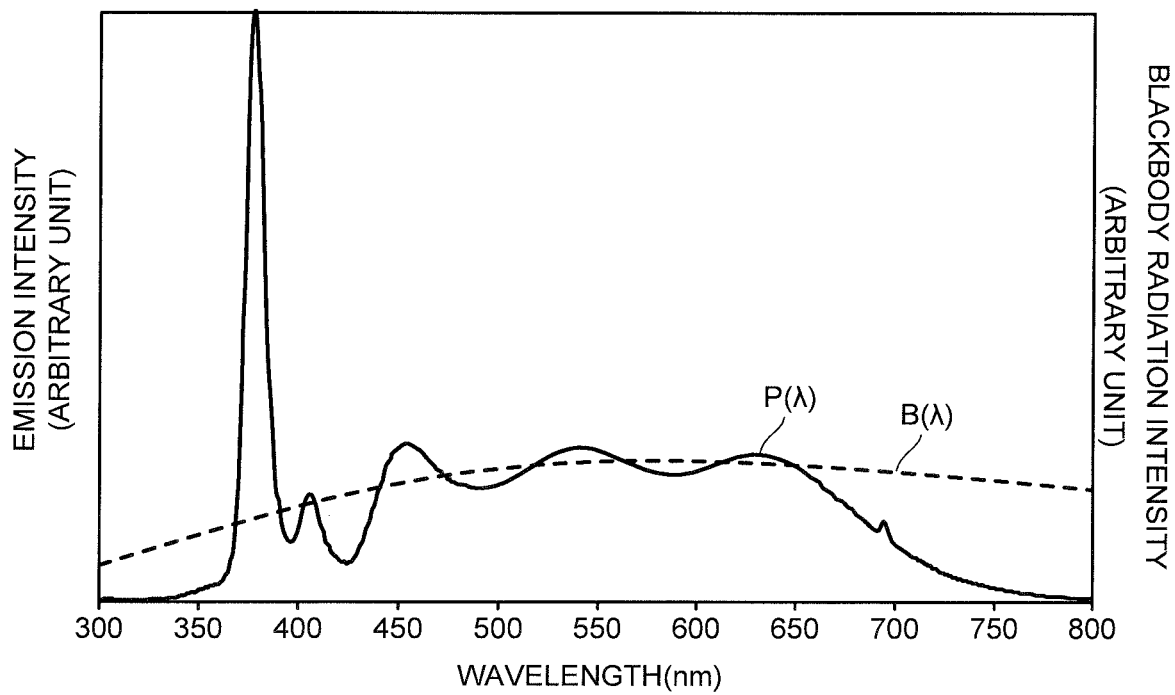
FIG. 13 is a chart illustrating emission spectra.

The output ratio between the first light emitting diode element and the second light emitting diode element was regulated so that the light emitted from the light source for myopia prevention article in Example 3 satisfied the formula: $\int B(\lambda)V(\lambda)d\lambda = \int P(\lambda)V(\lambda)d\lambda$ and satisfied a formula 2: $B(\lambda') \times 7.1 = P(\lambda')$. FIG. 13 illustrates the emission spectrum of the light emitted from the light source for myopia prevention article at this time and a black body radiation spectrum indicating the same color temperature as that of the above-described light.

The myopia prevention light source in Example 3 was disposed in a position 30 cm apart from an eye to be examined, and light emitted from the myopia prevention light source was regulated so that an irradiance in a wavelength region of 300 nm to 400 nm except 400 nm became 100 $\mu W/cm^2$ in an irradiated portion of the eye to be examined. Irradiating the eye to be examined with the above-described regulated light made it possible to confirm the suppression effect of the myopia indicated in the embodiment.

While certain embodiments of the present invention have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A method of using a light source for a myopia prevention article,
   the light source comprising:
   a light emitter configured to emit a light, the light giving an emission spectrum continuously extending from a first wavelength of not less than 360 nm and not more than 400 nm to a second wavelength of more than 400 nm, and the light having a color temperature of not less than 2600 K and not more than 7000 K; and
   the method comprising:
   irradiating a target with the light such that an irradiance in a wavelength region of 300 nm to 400 nm on the target is set at not less than 10 $\mu W/cm^2$ and not more than 400 $\mu W/cm^2$,
   wherein the irradiance is set by regulating at least one selected from the group consisting of
     an interval between the light emitter and the target; and
     a power supply voltage to be supplied to the light emitter,
   wherein the light emitter includes a first light emitting diode element configured to emit a first light, the first light giving a first emission spectrum having a first emission intensity peak in a wavelength region of not less than 360 nm nor more than 400 nm, and a second light emitting diode element configured to emit a second light, the second light giving a second emission spectrum having a second emission intensity peak in a wavelength region of more than 400 nm, and wherein the first and the second light emitting diode elements are respectively mounted on a first substrate and a second substrate, the first substrate and the second substrate being separated from each other.

2. The method according to claim 1, wherein the emission spectrum has a ratio a/b of an integrated value a of emission intensity of the light in a wavelength region of 300 nm to 400 nm to an integrated value b of emission intensity of the light in a wavelength region of 400 nm to 800 nm, the ratio a/b being more than 0.1 and less than 0.5.

3. The method according to claim 1, wherein the first wavelength is not less than 380 nm and not more than 400 nm.

4. The method according to claim 1, wherein a wavelength at which emission intensity of the light is maximum in a wavelength region of 400 nm or less is not less than 360 nm nor more than 400 nm.

5. The method according to claim 1, wherein the spectrum has a first emission intensity peak in a wavelength region of not less than 360 nm nor more than 400 nm and a second emission intensity peak in a visible region in a wavelength region of more than 400 nm, the second emission intensity peak is broader than the first emission intensity peak.

6. The method according to claim 1, wherein the first wavelength is 380 nm, and wherein the second wavelength is 700 nm.

7. The method according to claim 1, wherein the light satisfies the following formula 1:

$$\int B(\lambda)V(\lambda)d\lambda = \int P(\lambda)V(\lambda)d\lambda, \quad (1)$$

wherein $P(\lambda)$ represents an emission spectrum of the light, $B(\lambda)$ represents a black body radiation spectrum indicating a same color temperature as a color temperature of the light, and $V(\lambda)$ represents a spectrum of spectral luminous efficiency, and satisfies the following formula 2:

$$B(\lambda') \leq P(\lambda'), \quad (2)$$

wherein $P(\lambda')$ represents a maximum value of emission intensity of the light in a wavelength region of not less than 300 nm nor more than 400 nm and $B(\lambda')$ represents blackbody radiation intensity at a wavelength at which emission intensity of the light is the maximum value.

8. The method according to claim 7, wherein the light further satisfies the following formula 3:

$$B(\lambda') \leq P(\lambda') \leq B(\lambda') \times 15. \quad (3)$$

* * * * *